(12) United States Patent
Olovsson et al.

(10) Patent No.: US 12,264,306 B2
(45) Date of Patent: Apr. 1, 2025

(54) DEVICE FOR DISTRIBUTING A FLOW

(71) Applicant: Cytiva Sweden AB, Uppsala (SE)

(72) Inventors: Bjorn Olovsson, Uppsala (SE); Andreas Lundin, Uppsala (SE); Klaus Gebauer, Uppsala (SE); Tim Francois, Uppsala (SE); Kerstin Erickson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 830 days.

(21) Appl. No.: 17/296,711

(22) PCT Filed: Dec. 10, 2019

(86) PCT No.: PCT/EP2019/084321
§ 371 (c)(1),
(2) Date: May 25, 2021

(87) PCT Pub. No.: WO2020/126638
PCT Pub. Date: Jun. 25, 2020

(65) Prior Publication Data
US 2022/0025313 A1    Jan. 27, 2022

(30) Foreign Application Priority Data
Dec. 19, 2018    (GB) ..................... 1820690

(51) Int. Cl.
*C12M 1/00*    (2006.01)
(52) U.S. Cl.
CPC ............ *C12M 23/40* (2013.01); *C12M 23/26* (2013.01); *C12M 23/28* (2013.01)
(58) Field of Classification Search
None
See application file for complete search history.

(56) References Cited

U.S. PATENT DOCUMENTS 3,643,689 A    2/1972    Isreeli
4,821,996 A *  4/1989    Bellotti ................ F16K 11/027
                                                              251/9

(Continued)

FOREIGN PATENT DOCUMENTS

CN         1997553 A      7/2007
CN       101558259 A     10/2009

(Continued)

OTHER PUBLICATIONS

Japanese Office Action for JP Application No. 2021-534146 mailed Oct. 10, 2023 (20 pages).

(Continued)

*Primary Examiner* — Holly Kipouros
(74) *Attorney, Agent, or Firm* — Eversheds-Sutherland (US) LLP

(57) ABSTRACT

A flow distribution device for bioprocess systems, comprising: •—a flow distribution manifold (12; 112; 212; 312) comprising: •o at least four fluid connection tubes (14), wherein each fluid connection tube (14) comprises a first end (18) for fluid connection and an opposite second end (20) •o a central common compartment (30; 130; 230; 330) to which the second ends (20) of each of the fluid connection tubes (14) are connected, whereby the first ends (18) of each of the fluid connection tubes (14) can be in fluid communication with the central common compartment (30; 130; 230; 330) •—at least three pinching members (41) which are provided in connection with one fluid connection tube (14) of the flow distribution manifold (12; 112; 212; 312) each, wherein each of said pinching members (41) can be controlled into at least a first and a second position, wherein in the first position for each of the pinching members (41) the pinching member pinches one of the fluid connection tubes (14) such that fluid (Continued)

flow is prevented between the first end (18) and the second end (20) of this fluid connection tube (14).

13 Claims, 10 Drawing Sheets

(56) References Cited

U.S. PATENT DOCUMENTS

| | | | |
|---|---|---|---|
| 4,879,029 A | 11/1989 | Whitehead | |
| 6,554,806 B2 * | 4/2003 | Butterfield | A61M 39/285 251/9 |
| 10,130,948 B2 | 11/2018 | Cho et al. | |
| 10,550,360 B2 | 2/2020 | Grosch et al. | |
| 2014/0076454 A1 | 3/2014 | Kjar | |
| 2015/0259082 A1 * | 9/2015 | Goodwin | B65B 3/02 53/469 |
| 2017/0029144 A1 | 2/2017 | Kjar | |
| 2017/0342364 A1 | 11/2017 | Grosch et al. | |
| 2018/0258377 A1 * | 9/2018 | Shimase | F16K 7/06 |
| 2020/0061873 A1 * | 2/2020 | Zumbrum | B29C 39/36 |

FOREIGN PATENT DOCUMENTS

| | | |
|---|---|---|
| CN | 105814352 A | 7/2016 |
| CN | 106499841 A | 3/2017 |
| CN | 108757995 A | 11/2018 |
| DE | 102014226692 A1 | 6/2016 |
| EP | 1873520 A1 | 1/2008 |
| EP | 1948339 B1 | 7/2008 |
| JP | 63-078065 A | 4/1988 |
| JP | 2008139022 A | 6/2008 |
| JP | 2009511900 A | 3/2009 |
| JP | 2010-512490 A | 4/2010 |
| JP | 2010209962 A | 9/2010 |
| JP | 2015-518547 A | 7/2015 |
| JP | 2017-509834 A | 4/2017 |
| JP | 2018502302 A | 1/2018 |
| JP | 2022-514247 A | 2/2022 |
| WO | 96/12686 A2 | 5/1996 |
| WO | 97/12031 A1 | 4/1997 |
| WO | 9845629 A1 | 10/1998 |
| WO | 2008/073020 A1 | 6/2008 |
| WO | 2013130176 A1 | 9/2013 |
| WO | 2013/147697 A1 | 10/2013 |
| WO | 2015/095658 A1 | 6/2015 |
| WO | 2016096489 A1 | 6/2016 |

OTHER PUBLICATIONS

Chinese Office Action for CN Application No. 201980084557.9, dated Nov. 16, 2023 (12 pages).
Shi Xinhui, et al., "Simplified design of manifolds", Industrial Water & Wastewater, No. 4, pp. 60-65, Dec. 31, 1989 with English Translation.
Chinese Search Report for CN Application No. 201980084557.9, dated Nov. 9, 2023 (6 pages).
Indian Examination Report for IN Application No. 202117018222 mailed Jan. 10, 2023 (6 pages).
Search Report and Written Opinion for PCT/EP2019/084322, mailed Mar. 11, 2020 (14 pages).
GB Search Report and Examination Report for GB1820691.2, mailed Jun. 19, 2019 (6 pages).
Japanese Office Action and Search Report for JP Application No. 2021-534143 mailed Aug. 28, 2023 (11 pages).
PCT International Search Report and Written Opinion for PCT/EP2019/084321 mailed Apr. 28, 2020 (12 pages).
Great Britain Search Report for GB Application No. 1820690.4 mailed Jun. 19, 2019 (6 pages).

* cited by examiner

DEVICE FOR DISTRIBUTING A FLOW

CROSS REFERENCE TO RELATED APPLICATIONS

This application claims the priority benefit of PCT/EP2019/084321, filed on Dec. 10, 2019, which claims the benefit of Great Britain Application No. 1820690.4, filed on Dec. 19, 2018, the entire contents of which are incorporated by reference herein.

TECHNICAL FIELD OF THE INVENTION

The present invention relates to a flow distribution device, a flow distribution manifold, a bioprocess separation system and a single use flow path for bioprocess systems.

BACKGROUND

Pinch valve operated fluid delivery devices are for example used in single-use liquid handling systems applied in the bioprocess field. Single-use systems employ typically pre-sterilized components that are in fluid contact with the processing fluid. Such components are preferably made from incinerable plastics materials and are often disposed of after use to avoid cleaning prior to re-uses and related cleaning validation. By having the disposable components pre-sterilized and clean-room manufactured, all cleaning and cleaning validation prior to processing is also eliminated. Sterilization methods are usually gamma irradiation, E-beam sterilization, autoclaving but other methods exist. Pinch valves are often used with such disposable single-use components due to the simple and cost-effective principle. In manufacturing of biopharmaceuticals for example, such single-use systems are adapted for liquid handling in filtration and chromatography.

Due to the design principle of pinch valves, such devices suffer from dead volumes caused by the minimum length of tubing required when pinch valves are arranged in fluid manifolds. This problem arises especially at systems used in production scale employing higher flow rates, as this requires fluid lines of larger diameter and increased dimensions of tubing and components. Typically, tubing in production scale equipment has an inner diameter of 6.25 mm or larger. With such larger diameter tubing, an increasing risk for convective mixing of fluid in manifolds exists. In FIG. 1, such a device is schematically shown having six fluid ducts A connected to a manifold B. A pump P sucks fluid from the manifold B. A pinch valve C is disposed in each of the fluid ducts A. In FIG. 1, if the outer pinch valve on the left side is opened, fluid from this opened fluid duct flows through the manifold B through the pump P and is delivered to the system. However, on its way to the pump P, the fluid from the opened fluid duct will also reach into the space d in the other fluid ducts between the manifold B and the respective closed pinch valve C. Due to these dead volumes, the device cannot be rinsed effectively and there is a risk for contamination and carry over when running fractions and sequential protocols such as in chromatography.

SUMMARY

An object of the present invention is to provide a flow distribution arrangement with reduced risk for contamination and carry over.

A further object of the invention is to provide an easily mounted flow distribution device which is suitable in single-use systems.

This is achieved by a flow distribution device, a bioprocess separation system, a flow distribution manifold and a single-use flow path according to the independent claims.

According to one aspect of the invention a flow distribution device for bioprocess systems is provided, comprising:
 a flow distribution manifold comprising:
  at least four fluid connection tubes, wherein each fluid connection tube comprises a first end for fluid connection and an opposite second end, and wherein at least three of the fluid connection tubes comprise at least one flexible part which can be compressed for preventing fluid flow between the first and second end of the fluid connection tube (i.e. when compressed, it prevents flow between the first and second end of the fluid connection tube); and
  a central common compartment to which the second ends of each of the fluid connection tubes are connected, whereby the first ends of each of the fluid connection tubes can be in fluid communication with the central common compartment (i.e. when the flexible part is not compressed) and wherein the fluid connection tubes are entering the central common compartment from at least three different directions;
 wherein said flow distribution device further comprises
 at least three pinching members which are provided in connection with one fluid connection tube of the flow distribution manifold each, wherein each of said pinching members can be controlled into (are movable between) at least a first and a second position, wherein in the first position for each of the pinching members the pinching member pinches one of the fluid connection tubes such that fluid flow is prevented between the first end and the second end of this fluid connection tube and in the second position the pinching member is provided in a position such that fluid flow is allowed between the first end and the second end of the fluid connection tube.

According to another aspect of the invention, a bioprocess separation system is provided, comprising a separation device and at least one flow distribution device as defined above connected to an inlet and/or an outlet of the separation device.

According to another aspect of the invention a flow distribution manifold is provided comprising:
 at least four fluid connection tubes, wherein each fluid connection tube comprises a first end for fluid connection and an opposite second end, and wherein at least three of the fluid connection tubes comprise at least one flexible part which can be compressed for preventing fluid flow between the first and second end of the fluid connection tube (i.e. when compressed, it prevents flow between the first and second end of the fluid connection tube); and
 a central common compartment to which the second ends of each of the fluid connection tubes are connected, whereby the first ends of each of the fluid connection tubes can be in fluid communication with the central common compartment (i.e. when the flexible part is not compressed) and wherein the fluid connection tubes are entering the central common compartment from at least three different directions,
 wherein said flow distribution manifold is configured for being used in (or is used in) a flow distribution device as defined above.

According to another aspect of the invention, a single-use flow path is provided, configured to be used in (or being used in) a bioprocess separation system as described above and comprising a flow distribution manifold as described above configured to be used in a flow distribution device as described above.

Hereby a flow distribution device is provided, which will reduce the risk for contamination and carry over thanks to the design comprising a central common compartment into which the fluid connections are entering from different directions, i.e. there is a common compartment provided in the middle of the device. Herby a "distance" between different connections can be the same. Furthermore, cleaning of the device is much easier and more effective compared to a traditional pinch valve manifold as described in relation to FIG. 1. Furthermore, the flow distribution device according to the invention is suitable for use in single-use systems because the flow distribution manifold can easily be changed while the pinching members can be reused. The flow distribution manifold can be connected to a single-use flow path for a bioprocess separation system.

In one embodiment of the invention, at least five or at least six fluid connection tubes are provided in the flow distribution manifold.

In one embodiment of the invention, the fluid connection tubes are entering the central common compartment from at least four or five different directions.

In one embodiment of the invention, the second ends of the fluid connection tubes are connected to the central common compartment distributed around an enclosing wall of the central common compartment, which enclosing wall is enclosing an inner room of the central common compartment, wherein each of the fluid connection tubes can be in fluid communication with the inner room of the central common compartment and wherein the fluid connection tubes are entering the enclosing wall of the central common compartment from at least three or four or five different directions.

In one embodiment of the invention, distances between the second ends of each of the fluid connection tubes and a central point of the central common compartment will not differ by more than 3 or 2 or 1 times an inner diameter (ID) of the fluid connection tubes or a distance between the second end of each of the fluid connection tubes and a central point of the central common compartment is substantially the same for each fluid connection tube.

In one embodiment of the invention, a distance from the second end of at least one of the fluid connection tubes to a second end of an adjacent fluid connection tube is smaller than the distance between two pinching members configured for pinching said same two fluid connection tubes. Hereby the fluid connection tubes are spread around the central common compartment and not provided in parallel.

In one embodiment of the invention, the flow distribution device comprises either the same number of pinching members as the number of fluid connection tubes provided in the flow distribution manifold or one less, wherein one pinching member is provided in connection with each fluid connection tube or with each fluid connection tube except one, whereby either all fluid connection tubes or all except one can be pinched by a pinching member.

In one embodiment of the invention, said flow distribution manifold is a single-use component.

In one embodiment of the invention, said pinching members are configured for being controlled by a connected control system, whereby the positions of the pinching members can be controlled such that the first end of one of the fluid connection tubes can be fluidly connected with the first end of another one of the fluid connection tubes.

In one embodiment of the invention, the flow distribution device further comprises a holder for the flow distribution manifold, wherein said holder is configured for holding said flow distribution manifold in relation to the pinching members which can protrude into an interior of the holder and pinch said fluid connection tubes.

In one embodiment of the invention, a flow distribution device is connected to an inlet of the separation device, wherein one fluid connection tube of the flow distribution device is connected to the inlet of the separation device and at least three fluid connection tubes of the flow distribution device are connected to different fluid sources comprising fluids to be fed to the separation device.

In one embodiment of the invention, a flow distribution device is connected to an outlet of the separation device, wherein one fluid connection tube of the flow distribution device is connected to the outlet of the separation device and at least three fluid connection tubes of the flow distribution device are connected to different fraction collectors collecting different fractions from the separation device.

In one embodiment of the invention, the bioprocess separation system comprises a reusable part comprising the pinching members of the flow distribution device and at least one pump head and a single-use part comprising a single use flow path comprising the flow distribution manifold of the flow distribution device and the separation device.

In one embodiment of the invention, said single use flow path is pre-sterilized, e.g. by gamma irradiation.

BRIEF DESCRIPTION OF DRAWINGS

FIG. 2b is a cross section of the flow distribution device as shown in FIG. 2a.

DETAILED DESCRIPTION OF EMBODIMENTS

Figure 1:
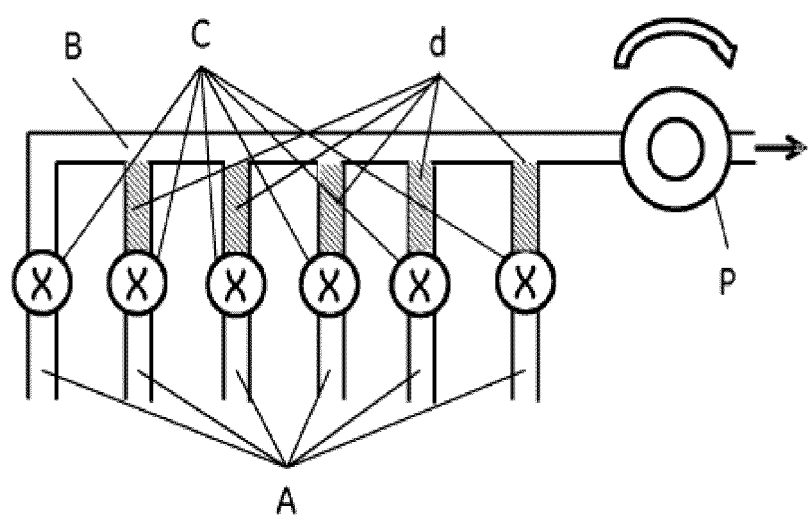
FIG. 1 shows schematically a device for delivery of fluid according to prior art.
Figure 2A:
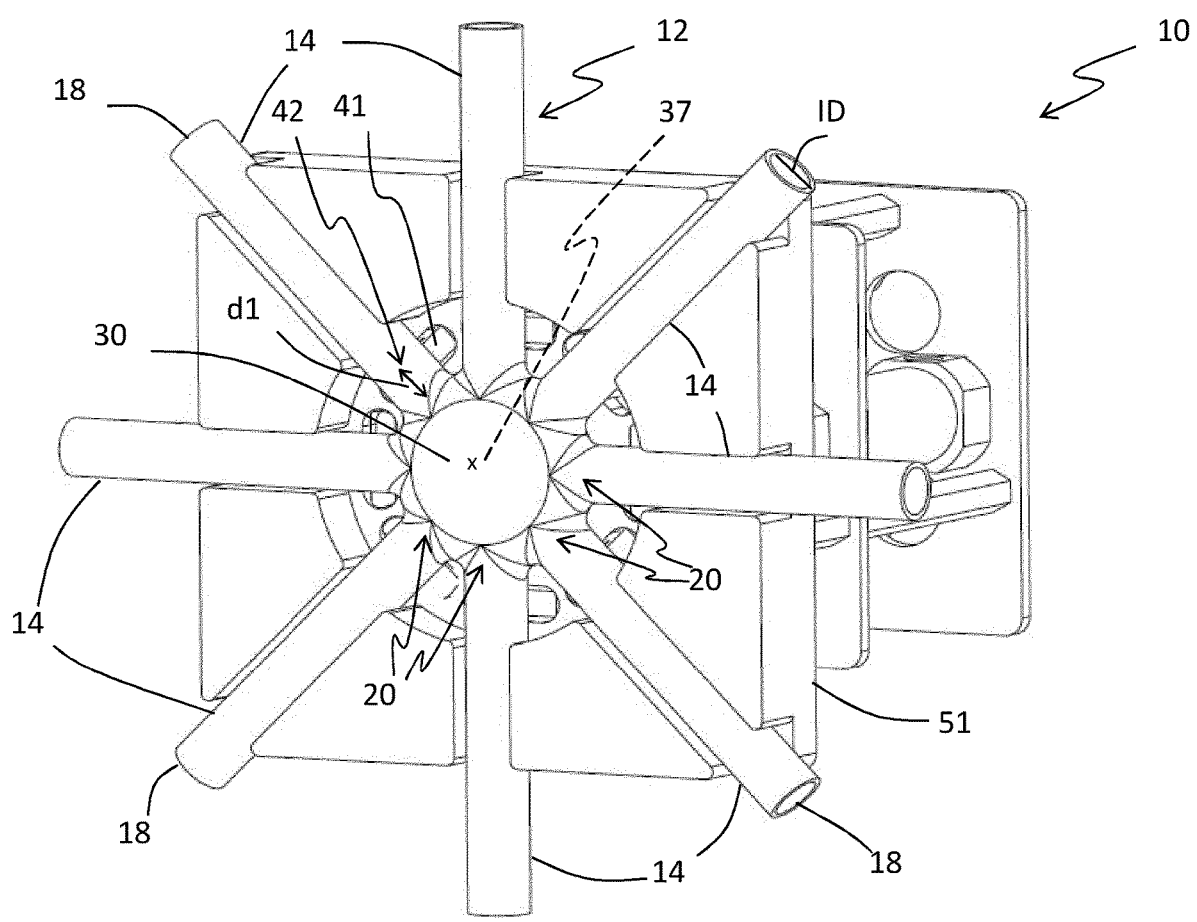
FIG. 2a is a perspective view of a flow distribution device according to one embodiment of the invention.
Figure 2B:
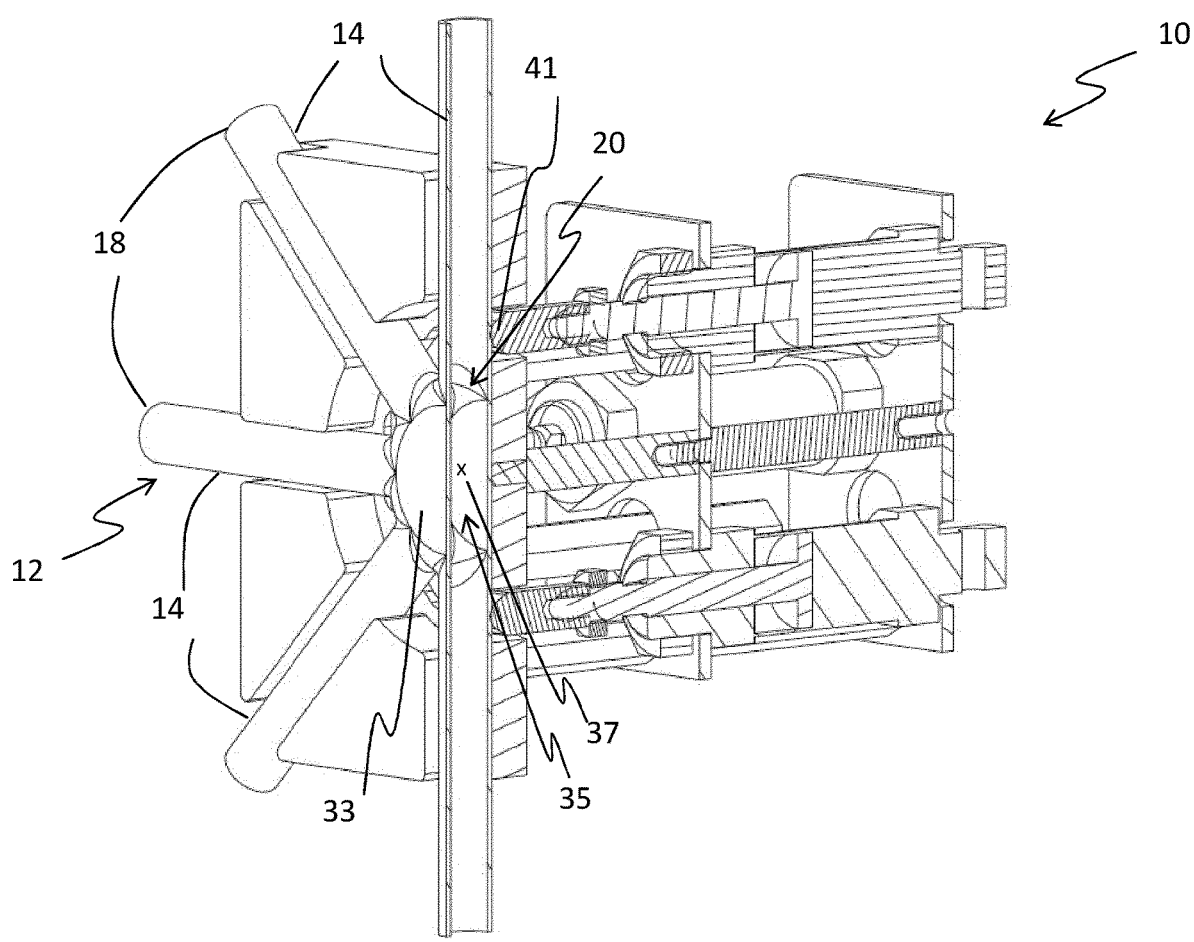
Figure 2C:
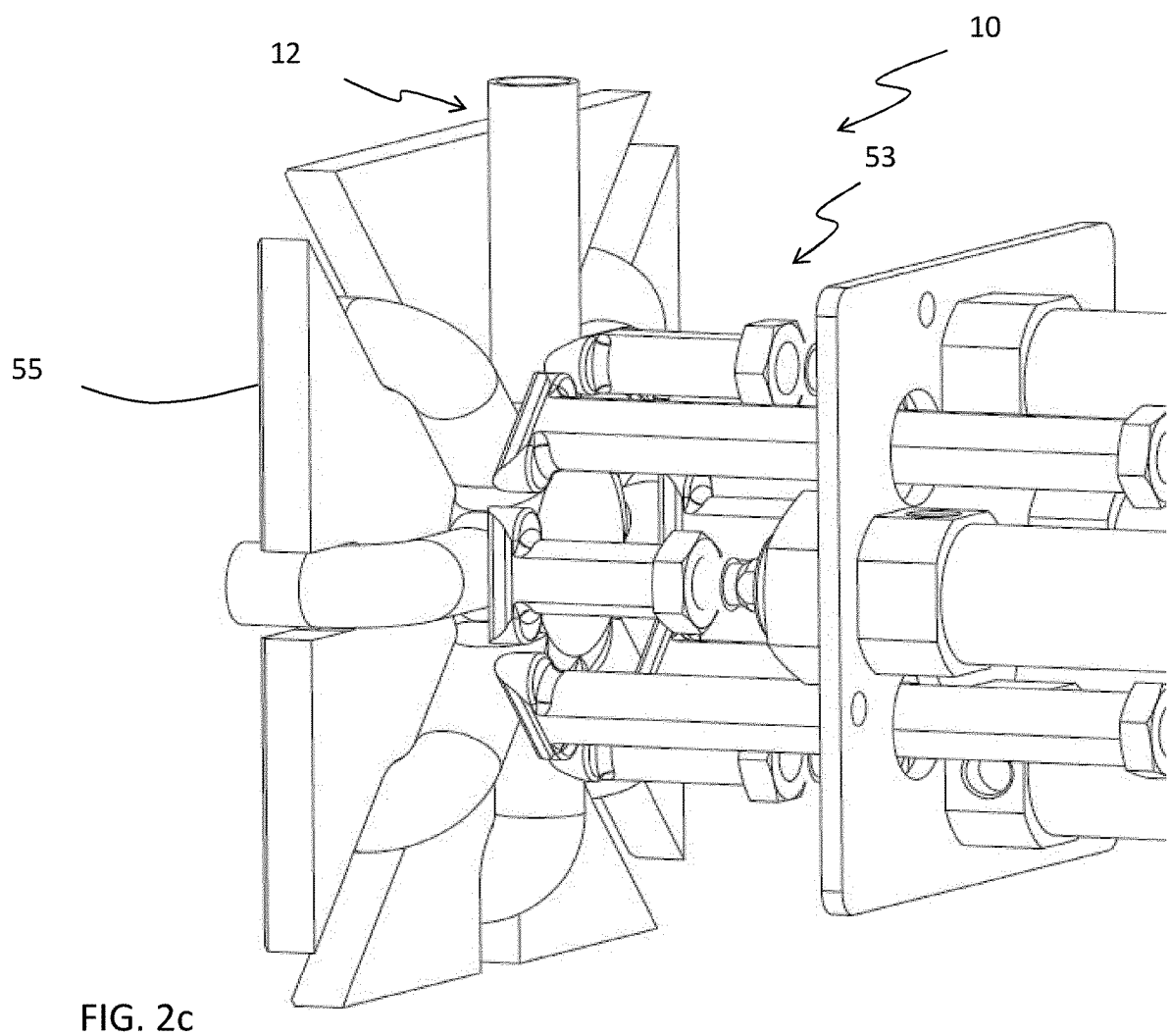
FIG. 2c is a perspective view of the flow distribution device as shown in FIGS. 2a and 2b but from another side of the device.
Figure 2D:
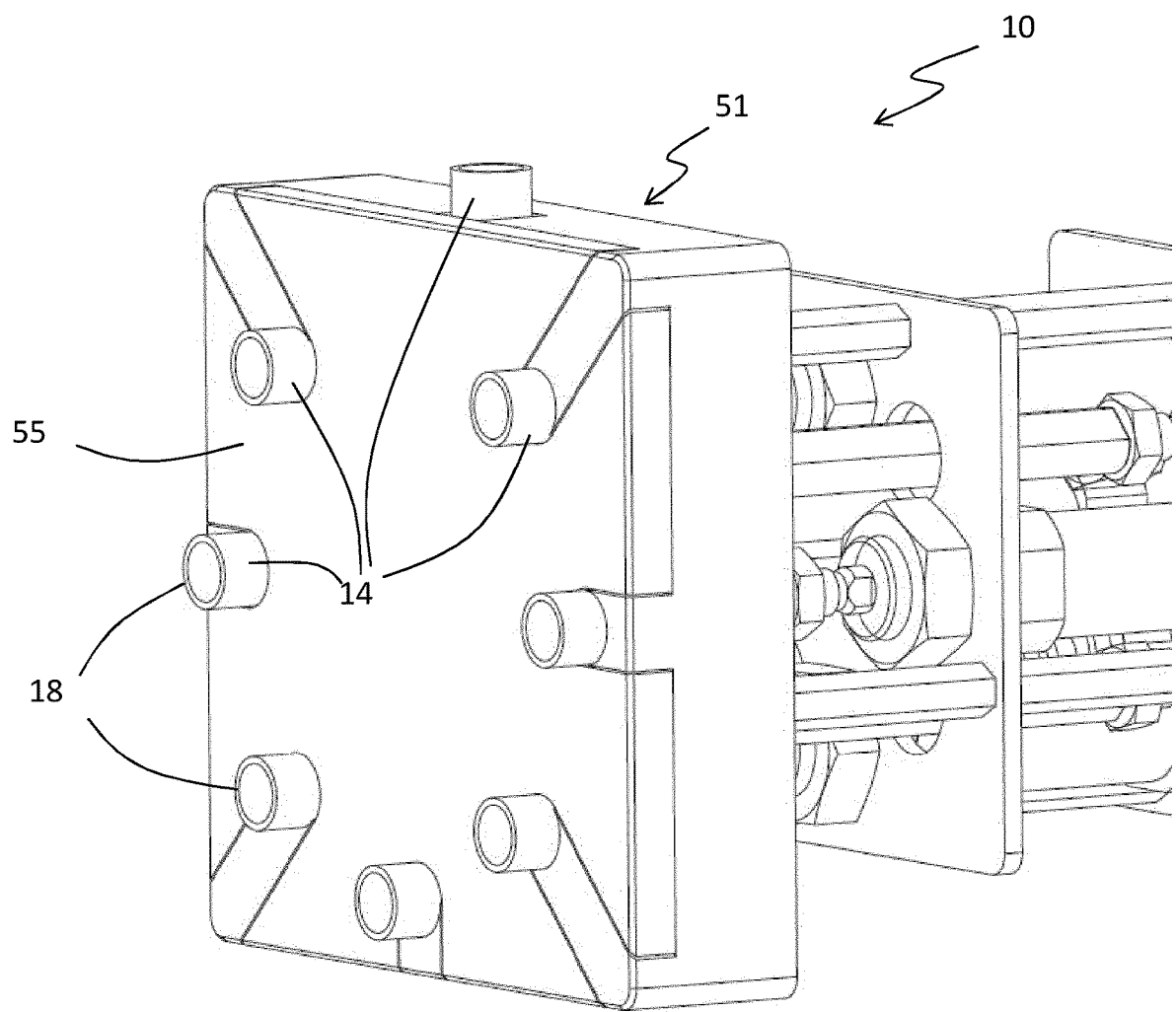
FIG. 2d is a perspective view of the flow distribution device as shown in FIGS. 2a-2c but with a cover provided.
Figure 3A:
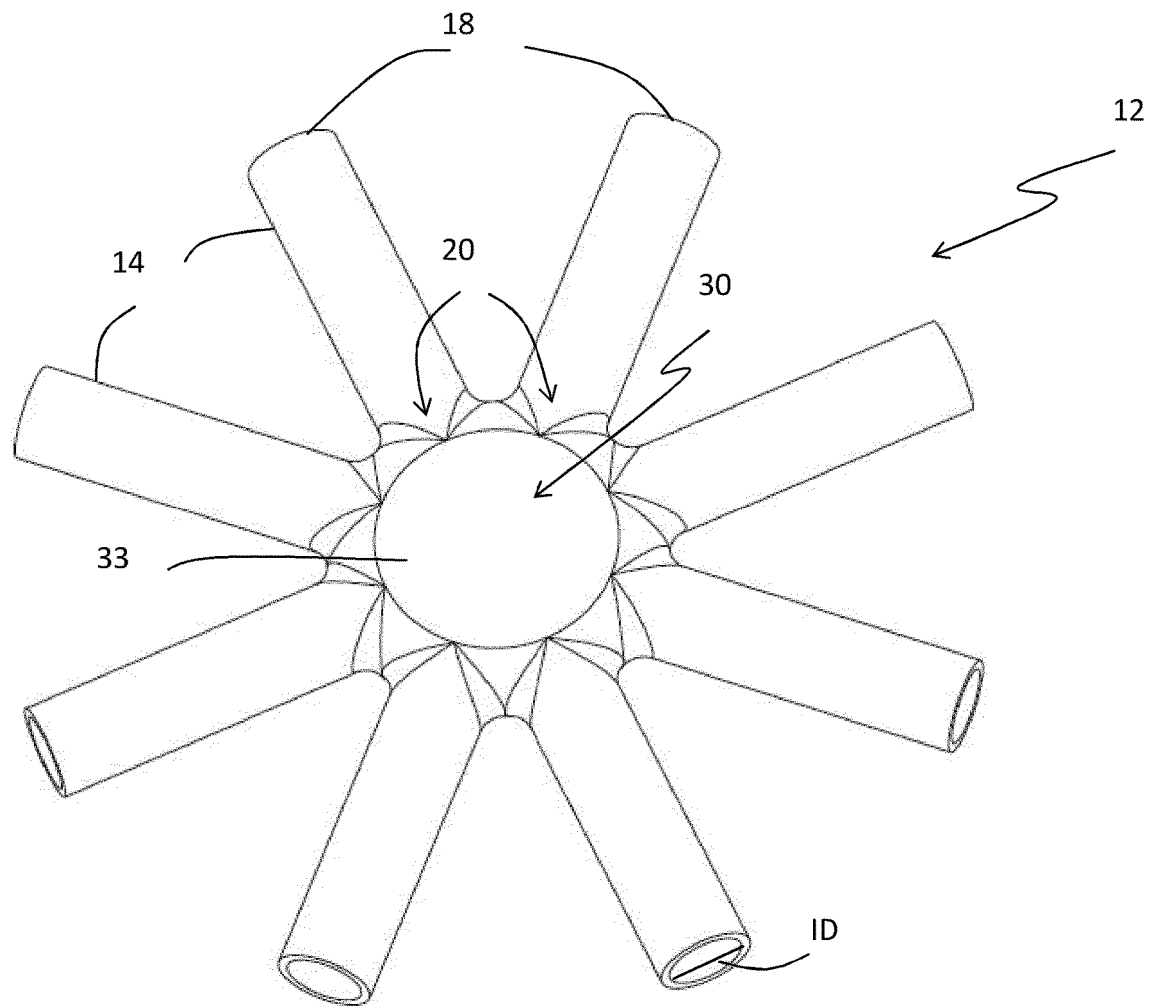
FIG. 3a shows schematically a flow distribution manifold according to one embodiment of the invention.

FIGS. 2a-2d show different perspective and cross sectional views of a fluid distribution device 10 according to one embodiment of the invention. The fluid distribution device 10 comprises one part which can be a single-use part. This is called a fluid distribution manifold 12 and comprises at least four fluid connection tubes 14. In another embodiment the fluid distribution manifold comprises at least five or at least six fluid connection tubes 14. In FIGS. 3a-3d four different embodiments of fluid distribution manifolds 12; 112; 212; 312 are shown. The fluid distribution manifold in FIG. 3a is the same embodiment as the fluid distribution manifold 12 shown in FIGS. 2a-2d. Each fluid connection tube 14 comprises a first end 18 for fluid connection and an opposite second end 20. In this embodiment eight fluid connection tubes 14 are shown, however the number of fluid connection tubes can of course be different. In one embodiment of the invention at least all fluid connection tubes 14 except one comprise at least one flexible part which can be compressed for preventing fluid flow between the first and second end 18, 20 of the fluid connection tube 14. Of course also all fluid connection tubes can comprise at least one flexible part. Optionally the entire fluid connection tubes 14 are flexible. It can also be expressed, as in the claims, that at least three of the fluid connection tubes 14 when there are at least four fluid connection tubes 14 comprise at least one flexible part. The compression is related to pinching members provided in the fluid distribution device as will be further described below. In the embodiments of the fluid distribution manifold as shown in FIGS. 2a-2d and in FIGS. 3a-3d, seven or eight fluid connection tubes 14 are shown which are all flexible tubes.

According to the invention, the fluid distribution manifold 12 further comprises a central common compartment 30 to which the second ends 20 of each of the fluid connection tubes 14 are connected, whereby the first ends 18 of each of the fluid connection tubes 14 can be in fluid communication with the central common compartment 30. Furthermore according to the invention the fluid connection tubes 14 are entering the central common compartment 30 from at least three different directions. In another embodiment of the invention the fluid connection tubes 14 are entering the central common compartment 30 from at least four or at least five different directions. In the embodiment shown in FIGS. 2a-2d all the fluid connection tubes 14 are entering the central common compartment 30 from different directions and the fluid distribution manifold 12 has a star like configuration with the fluid connection tubes 14 pointing away from the central common compartment 30 in different directions. In the embodiments shown in FIG. 2 and FIGS. 3a-3c the fluid connection tubes 14 are all provided in one and the same plane when entering into the central common compartment 30 but they could as well be provided in different planes as shown in FIG. 3d, i.e. the second ends 20 of the fluid connection tubes 14 can be connected to the central common compartment 30 distributed around an enclosing wall 33 of the central common compartment 30, which enclosing wall 33 is enclosing an inner room 35 of the central common compartment 30, wherein each of the fluid connection tubes 14 can be in fluid communication with the inner room 35 of the central common compartment 30 and wherein the fluid connection tubes 14 are entering the enclosing wall 33 of the central common compartment 30 from at least three or four or five different directions. In the embodiments of the invention shown in FIGS. 2 and 3 the fluid connection tubes are entering the enclosing wall 33 of the central common compartment 30 from seven or eight different directions.

The flow distribution device 10 further comprises at least three pinching members 41 which are provided in connection with one fluid connection tube 14 of the flow distribution manifold 12 each. In the embodiment of the invention as shown in FIGS. 2a-2d one pinching member 41 is provided for each fluid connection tube 14, i.e. eight pinching members 41 are provided in the flow distribution device 12. However in another embodiment the number of pinching members 41 can instead be one less or optionally even two less than the number of fluid connection tubes 14, i.e. one or optionally even two of the fluid connection tubes 14 need not to be pinched if the others can be pinched.

Each of said pinching members 41 can be controlled into at least a first and a second position, wherein in the first position for each of the pinching members 41 the pinching member 41 pinches one of the fluid connection tubes 14 such that fluid flow is prevented between the first end 18 and the second 20 of this fluid connection tube 14 and in the second position the pinching member 41 is provided in a position such that fluid flow is allowed between the first end 18 and the second end 20 of the fluid connection tube 14.

The pinching members 41 can be controlled by different types of mechanical arrangement or pressurized air as is well known in the art. The pinching members 41 can also be configured for being controlled by a connected control system, whereby the positions of the pinching members 41 can be controlled such that the first end 18 of one of the fluid connection tubes 14 can be fluidly connected with the first end 18 of another one of the fluid connection tubes 14. In one embodiment of the invention the first end 18 of any one of the different fluid connection tubes 14 can be connected with the first end 18 of any one of the other fluid connection tubes 14.

The pinching members 41 are suitably provided in a position such that they pinch the fluid connection tubes 14 close to the second ends 20 of the fluid connection tubes 14. The distance d1 between a pinching position 42 on the fluid connection tubes 14 and the second end 20 of the fluid connection tube 14 can for example be less than four or less than three or less than two fluid connection tube 14 inner diameter ID.

In some embodiments of the invention the distances between the second ends 20 of each of the fluid connection tubes 14 and a central point 37 of the central common compartment 30 will not differ by more than 3 or 2 or 1 times an inner diameter, ID, of the fluid connection tubes 14. In the embodiments as shown in FIGS. 2a-2d and in FIGS. 3a-3d the central common compartment 30; 130; 230; 330 is symmetrical and the fluid connection tubes 14 are positioned symmetrical around the central common compartment 30 at substantially the same distance from a central point 37; 137; 237 of the central common compartment 30, i.e. a distance between the second end 20 of each of the fluid connection tubes 14 and a central point 37 of the central common compartment 20 is substantially the same for each fluid connection tube 14.

A difference from prior art flow delivery manifolds with pinch valves is that in prior art the fluid connections were provided in parallel while in this new invention at least some of the fluid connection tubes are provided in different directions, i.e. at least some of the fluid connection tubes 14 are spread out from the central common compartment 30. Hereby a distance from the second end 20 of at least one of the fluid connection tubes 14 to a second end 20 of an adjacent fluid connection tube 14 is smaller than the distance between two pinching members 41 configured for pinching said same two fluid connection tubes 14.

The flow distribution manifold 12; 112; 212; 312 can suitably be a single-use component. It can be molded in one or more pieces from a flexible material. Alternatively the central common compartment 30 can be provided in a more rigid material and the fluid connection tubes 14 can be provided in a flexible material and molded to the central common compartment 30. The flow distribution manifold 12; 112; 212; 312 can be pre-sterilized for example by gamma radiation or other sterilization methods, optionally together with other parts of a single-use flow path to be used for example in a bioprocess separation system, such as a chromatography system or a filter system as will be further described below.

Figure 4:
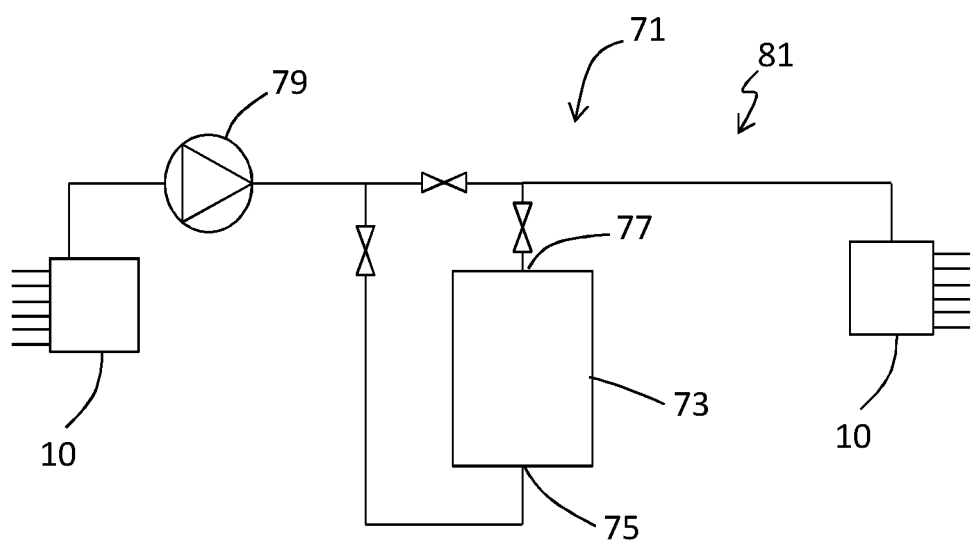
FIG. 4 shows schematically a bioprocess separation system in which a flow distribution device according to the invention can be used.

Another part of the flow distribution device 10 can be a reusable part and this part comprises the pinching members 41 and suitably also a holder 51. Said holder 51 is configured for holding said flow distribution manifold 12; 112; 212; 312 in relation to the pinching members 41 which can protrude into an interior 53 of the holder 51 and pinch said fluid connection tubes 14. Herby the fluid connection tubes 14 can be positioned inside the holder 51 such that each pinching member 41 is provided in a position in the holder 51 such that it can pinch one each of the fluid connection tubes 14. Furthermore a cover 55 is suitably provided covering the fluid connection tubes 14 from the side of the fluid connection tubes 14 opposite to the side where the pinching members 41 are provided. Hereby, the pinching members 41 can pinch the fluid connection tubes 14 against the cover 55. The cover 55 may have openings 57 for the first ends 18 of the fluid connection tubes 14. In the embodiment shown in FIGS. 2a-2d, one opening 57' is provided in a side of the holder 51 and the other openings 57 are provided in the cover 55. Hereby, the fluid connection tube 14, which is protruding out through the opening 57' in the side of the holder 51, can suitably be connected to an inlet 75 or an outlet 77 of a separation device 73 of a bioprocess separation system 71, such as a chromatography column of a chromatography system or a filter of a filter system as is shown in FIG. 4. The fluid connection tubes 14 protruding out through the openings in the cover 55 can then be connected to different fluid sources for feeding different fluids into the separation device 73 or to different fraction collection devices for receiving different fractions out from the separation device 73.

The present invention also relates to a bioprocess separation system 71 as schematically shown in FIG. 4, such as a chromatography system or a filter system, which comprises one or more fluid distribution devices 10 as described above. One fluid distribution device 10 can be connected to an inlet 75 of a separation device 73 provided in the bioprocess separation system 71 and/or one fluid distribution device 10 can be connected to an outlet 77 of the separation device 73. The separation device 73 can for example be a chromatography column or a filter. At least one pump 79 is also provided in the bioprocess separation system 71. Other components such as valves and sensors are normally also provided in the bioprocess separation system 71 but will not be described in further detail here. A single-use flow path 81 comprising flow paths, the flow distribution manifold 12; 112; 212; 312 according to the invention and optionally also the separation device 73 is also part of the present invention, i.e. the flow distribution manifold 12; 112; 212; 312 can be connected to other flow paths of a bioprocess separation system and be pre-sterilized for easy connection and exchange in a bioprocess separation system 71. Reusable parts of the bioprocess separation system 71 are for example pump heads 79 and the pinching members 41 of the flow distribution device 10.

Figure 3B:
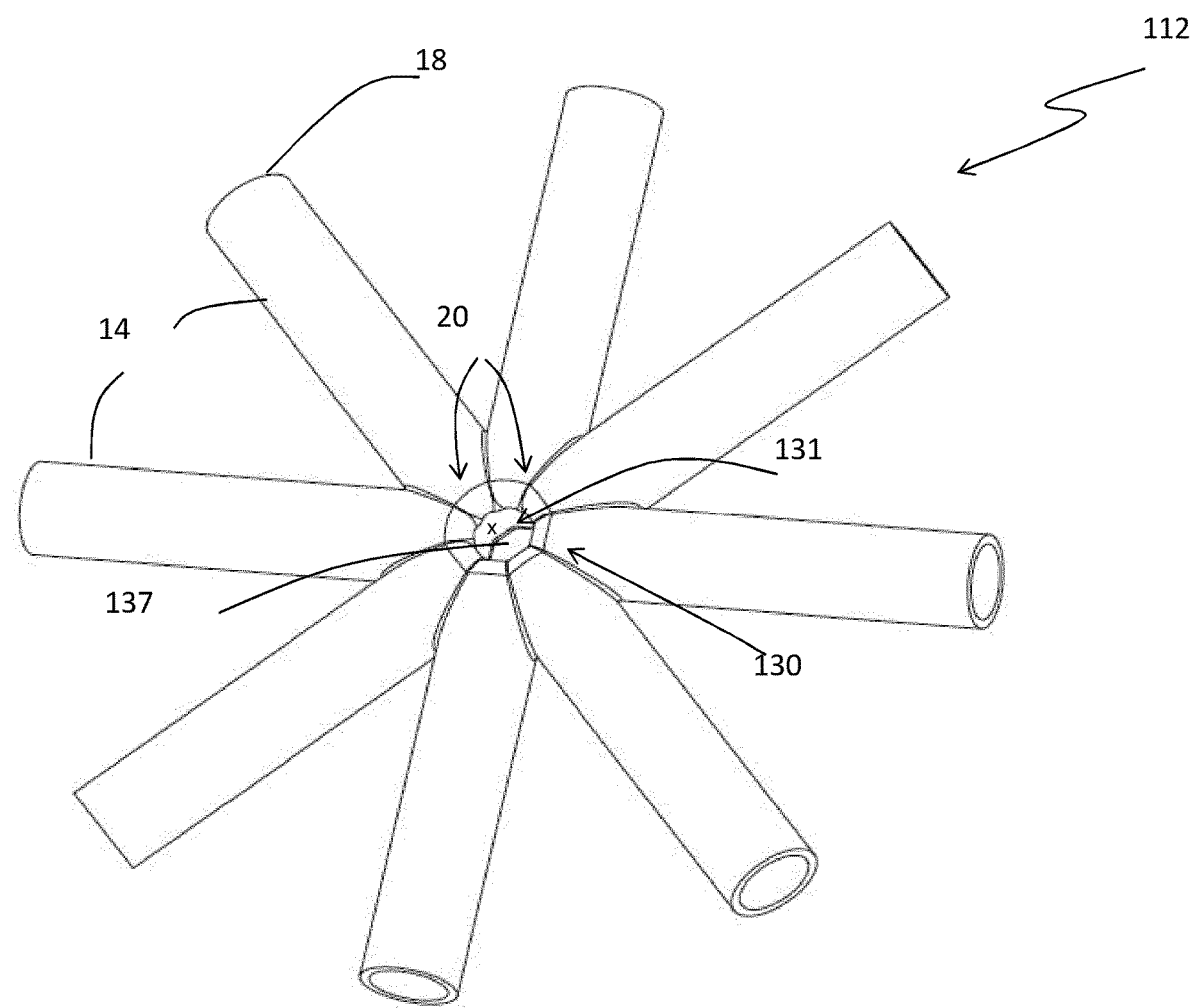
FIG. 3b shows schematically a flow distribution manifold according to another embodiment of the invention.
Figure 3C:
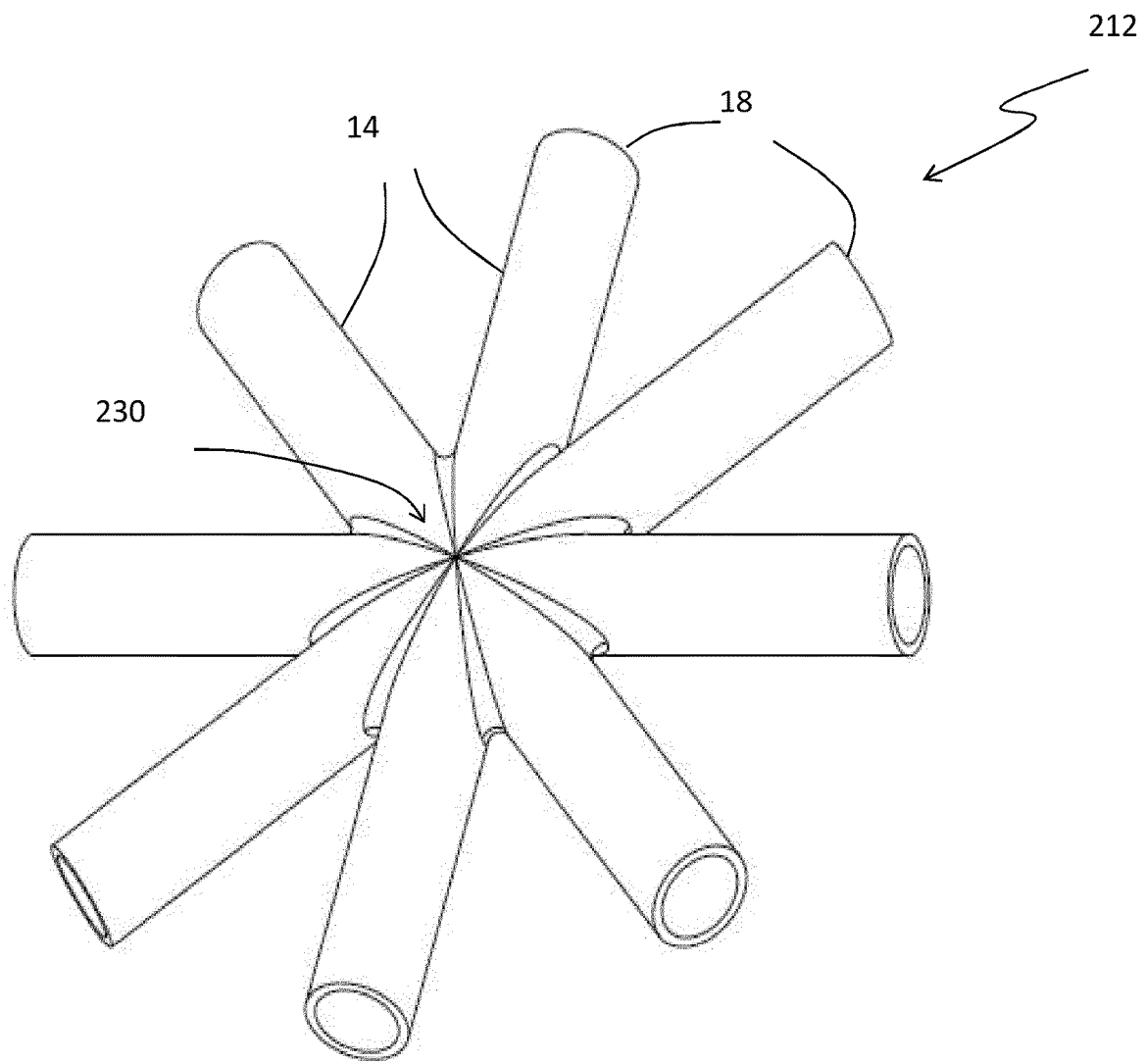
FIG. 3c shows schematically a flow distribution manifold according to another embodiment of the invention.
Figure 3D:
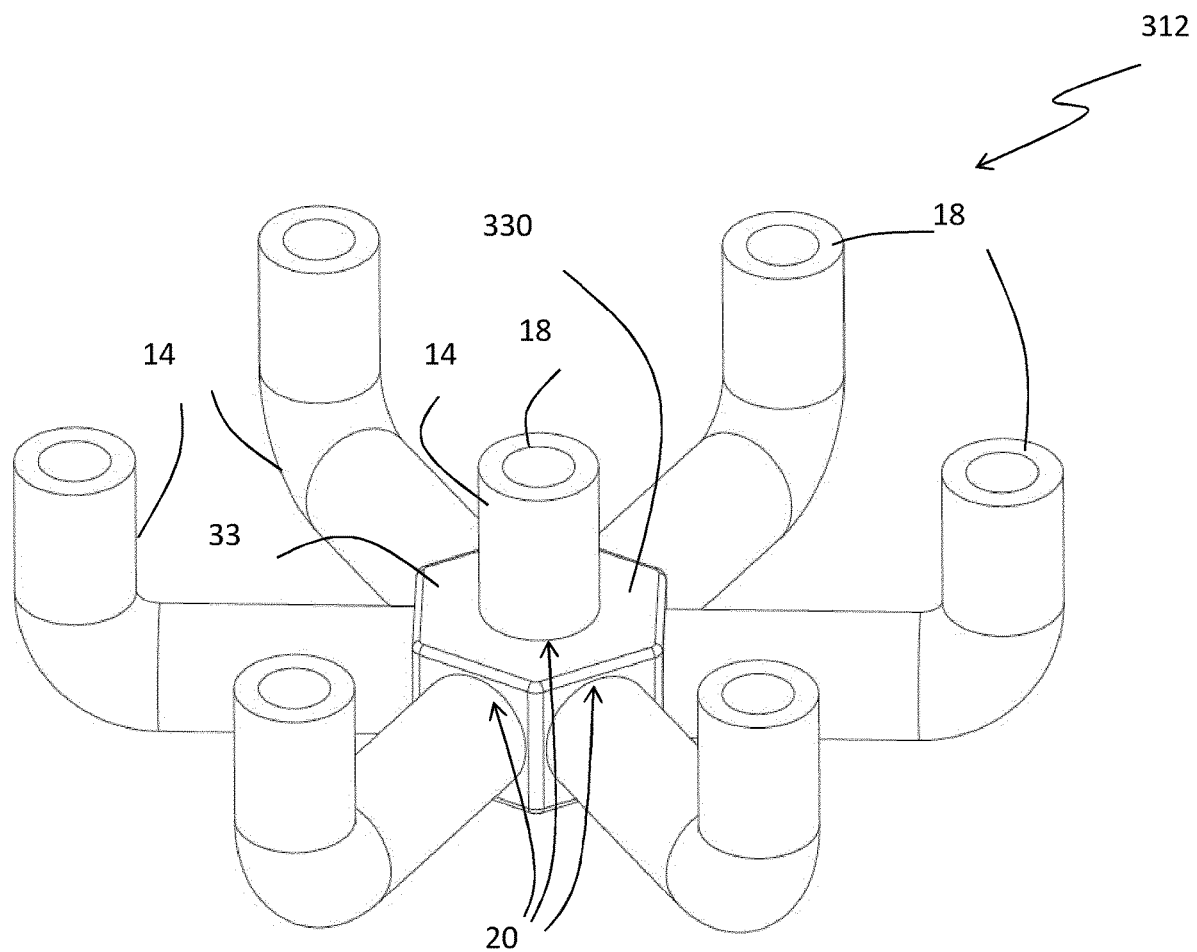
FIG. 3d shows schematically a flow distribution manifold according to another embodiment of the invention.

In FIGS. 3b, 3c and 3d three alternative configurations of a flow distribution manifold 112, 212; 312 according to the invention are shown. The flow distribution manifold 112 in FIG. 3b comprises a central common compartment 130 having an opening 131 in the middle. Hereby a central point 137 which is referred to in the description and in the claims is in this embodiment not inside an inner room of the central common compartment but in the middle of the opening 131. The inner room of the central common compartment 130 is hereby annular and is encircling the opening 131. It could be advantageous to have this opening 131 in the middle because the volume of the central common compartment 130 can then be decreased. In FIG. 3c an alternative way of molding the fluid connection tubes 14 to the central common compartment 230 is illustrated. The flow distribution manifold 312 in FIG. 3d comprises seven fluid connection tubes 14 whereof six of them are provided in one and the same plane when entering a central common compartment 330 of the flow distribution manifold 312 and one of the fluid connection tubes 14 is entering the central common compartment 330 in another plane. Hereby the second ends 20 of the fluid connection tubes 14 are distributed around a circumference of an enclosing wall 33 of the central common compartment 330.

As discussed above the flow distribution manifold is suitable for single-use applications. The flow distribution manifold and optionally a single use flow path to which it can be connected can be pre-sterilized by for example gamma radiation and can be provided with aseptic connectors for aseptic connection in a system.

The single-use technology (SUT) is important in the bioprocess industry in order to reduce production cost, increase production throughput and quality and to increase safety. With single-use processing technology and equipment, wetted parts that are in contact with the process fluid and drug product during processing, such as for example fluid storage vessels, tubing, separation equipment etc., are provided as clean and ready to use consumables which are to be installed and used for a specific process, product or over a limited time only and to be disposed thereafter.

SUT consumables are typically produced, configured and packaged in clean room environments to avoid contamination with microorganisms, particulates etc. SUT wetted parts can further be provided clean and pre-sterilized, thus allowing for aseptic and/or sterile processing, hereby reducing above mentioned risks relevant for product, operator or patient safety. Typically, SUT wetted parts are subjected to a sterilizing gamma irradiation treatment prior to use in the biomanufacturing process, and when doing so they are deployed as 'pre-sterilized' at the point of use. This may involve providing the consumable with a formal and validated sterile claim after the sterilizing treatment, however, it may alternatively involve providing a consumable that has undergone a sterilizing treatment but is provided without a formal sterile claim. With controlled and rigorous manufacturing conditions, SUT consumables may also be deployed non-sterile and/or with treatments that controls the state and condition of the consumable. Hereby, contamination levels by microorganisms, generally called 'bioburden', or levels of contamination or presence of contaminating substances or particles may be controlled and maintained within pre-defined levels.

The advantage of using single-use technology (SUT) fluid handling equipment is primarily that cross-contamination in between production batches and campaigns is eliminated when the SUT equipment is used for a single drug product only. The SUT equipment is disposed of after use, which can be after a single run, batch or campaign comprising multiple runs and batches. When providing SUT equipment pre-sterilized or by other means bioburden controlled, initial cleaning and sanitization (for example by contacting the flow path with sodium hydroxide solutions) or sterilization can be avoided. This enables a LEAN manufacturing approach, because time consuming, costly and non-value adding steps can be omitted. When using the SUT for a single run or batch only, even cleaning post-use may be omitted. The elimination of cleaning procedures and required cleaning fluids further reduces clean water requirements to prepare cleaning solutions in the first place, fluid handling and waste treatment, which translates to reduced facility size and complexity.

Single-use equipment may be provided with fluid connectors that enable closed processing and thereby protect the process fluid line and/or the operator and environment from contamination or exposure to hazardous substances. Alternatively, fluid connectors may be providing aseptic connectivity features, hereby providing strict and complete closure of the fluid lines. When using aseptic connectors or disconnectors, sterility of a fluid line, two connected lines or components, or two disconnected lines or components can be maintained, provided that the fluid lines or components involved in the operation have been provided sterile. With these features, SUT equipment allows not only for more efficient processing, it may also allow for reducing requirements on classification and containment of facilities, thereby reducing cost and risk for contamination or infection of the process fluid and drug product, and/or contamination and infection of the process environment, facility or the operator.

SUT systems provide higher flexibility in (re-)configuring a manufacturing facility and adapting it to different processes and products by design, i.e. through the reduced need for fixed installations compared to traditional processing systems and installations, which for example required auxiliary systems for CIP (Cleaning in Place) and SIP (Sterilization in place). Nowadays, SUT equipment and SUT processing regimes are therefore available or are being made available for the majority of all types of equipment and/or unit operations, among them bioreactors for cell culture or fermentation, buffer bags for liquid storage, tubing and pumps for liquid transfer and filling operations, filters, chromatography columns and related systems for separations.

With these features, SUT equipment does provide improved efficiency, safety and convenience compared to traditional installations and systems. Traditional installations and systems for processing are typically made from stainless steel and/or plastic and are not produced under controlled (or clean room) conditions reducing bioburden. Traditional systems are typically cleaned in place (CIP), sometimes also sterilized in place (SIP), which not only requires auxiliary installations, equipment and fluids, but involves also substantial time for validation, execution, and quality control of CIP and SIP procedures. The size, cost and complexity of facilities relying on traditional equipment and installations is significantly larger compared to production facilities deploying SUT. SUT facilities and processes can be planned, built and started up in significantly shorter time compared to traditional manufacturing technology, and SUT reduces capital investments and financial risk associated with a typically highly dynamic portfolio of drug products as well as risk and uncertainty related to the testing and approval of drug candidates and their product demand.

The invention claimed is:

1. A flow distribution device for bioprocess systems, comprising:
   a flow distribution manifold comprising:
      at least four fluid connection tubes, wherein each fluid connection tube comprises a first end for fluid connection and an opposite second end, and wherein at least three of the fluid connection tubes comprise at least one flexible part which can be compressed for preventing fluid flow between the first and second end of the fluid connection tube; and
      a central common compartment to which the second ends of each of the fluid connection tubes are connected, whereby the first ends of each of the fluid connection tubes can be in fluid communication with the central common compartment and wherein the fluid connection tubes are entering the central common compartment from at least three different directions;
   wherein said flow distribution device further comprises
      at least three pinching members positioned within a cavity surrounding the central compartment which are provided in connection with one fluid connection tube of the flow distribution manifold each, wherein each of said pinching members can be controlled into at least a first and a second position, wherein in the first position for each of the pinching members the pinching member pinches one of the fluid connection tubes such that fluid flow is prevented between the first end and the second end of this fluid connection tube and in the second position the pinching member is provided in a position such that fluid flow is allowed between the first end and the second end of the fluid connection tube; and
      wherein a distance from the second end of at least one of the fluid connection tubes to a second end of an adjacent fluid connection tube is smaller than the distance between two pinching members configured for pinching the same two fluid connection tubes.

2. The flow distribution device according to claim 1, wherein at least five or at least six fluid connection tubes are provided in the flow distribution manifold.

3. The flow distribution device according to claim 1, wherein the fluid connection tubes are entering the central common compartment from at least four or five different directions.

4. The flow distribution device according to claim 1, wherein the second ends of the fluid connection tubes are connected to the central common compartment distributed around an enclosing wall of the central common compartment, which enclosing wall is enclosing an inner room of the central common compartment, wherein each of the fluid connection tubes can be in fluid communication with the inner room of the central common compartment and wherein the fluid connection tubes are entering the enclosing wall of the central common compartment from at least three or four or five different directions.

5. The flow distribution device according to claim 1, wherein distances between the second ends of each of the fluid connection tubes and a central point of the central common compartment is no more than 3 or 2 or 1 times an inner diameter of the fluid connection tubes or wherein a distance between the second end of each of the fluid connection tubes and a central point of the central common compartment is substantially the same for each fluid connection tube.

6. The flow distribution device according to claim 1, wherein the flow distribution device comprises either the same number of pinching members as the number of fluid connection tubes provided in the flow distribution manifold or one less, wherein one pinching member is provided in connection with each fluid connection tube or with each fluid connection tube except one, whereby either all fluid connection tubes or all except one can be pinched by a pinching member.

7. The flow distribution device according to claim 1, wherein said flow distribution manifold is a single-use component.

8. The flow distribution device according to claim 1, wherein said pinching members are configured for being controlled by a connected control system, whereby the positions of the pinching members can be controlled such that the first end of one of the fluid connection tubes can be fluidly connected with the first end of another one of the fluid connection tubes.

9. The flow distribution device according to claim 1, further comprising a holder for the flow distribution manifold, wherein said holder is configured for holding said flow distribution manifold in relation to the pinching members which can protrude into an interior of the holder and pinch said fluid connection tubes.

10. A bioprocess separation system comprising a separation device and at least one flow distribution device according to claim 1 connected to an inlet and/or an outlet of the separation device.

11. The bioprocess separation system according to claim 10, wherein the flow distribution device is connected to an inlet of the separation device, wherein one fluid connection tube of the flow distribution device is connected to the inlet of the separation device and at least three fluid connection tubes of the flow distribution device are connected to different fluid sources comprising fluids to be fed to the separation device.

12. The bioprocess separation system according to claim 10, wherein a flow distribution device is connected to an outlet of the separation device, wherein one fluid connection tube of the flow distribution device is connected to the outlet of the separation device and at least three fluid connection tubes of the flow distribution device are connected to different fraction collectors collecting different fractions from the separation device.

13. The bioprocess separation system according to claim 10, wherein the bioprocess separation system comprises a reusable part comprising the pinching members of the flow distribution device and at least one pump head and a single-use part comprising a single use flow path comprising the flow distribution manifold of the flow distribution device and the separation device.

* * * * *